(12) United States Patent  
Fountain

(10) Patent No.: US 10,292,692 B1  
(45) Date of Patent: May 21, 2019

(54) PANNUS APRON AND METHOD FOR ACCESSING A SURGICAL SITE

(71) Applicant: Ginger Fountain, Trinity, NC (US)

(72) Inventor: Ginger Fountain, Trinity, NC (US)

(*) Notice: Subject to any disclaimer, the term of this patent is extended or adjusted under 35 U.S.C. 154(b) by 3 days.

(21) Appl. No.: 15/656,339

(22) Filed: Jul. 21, 2017

Related U.S. Application Data

(60) Provisional application No. 62/375,729, filed on Aug. 16, 2016.

(51) Int. Cl.
  *A61B 17/02* (2006.01)
  *A61B 17/00* (2006.01)

(52) U.S. Cl.
  CPC .... *A61B 17/02* (2013.01); *A61B 2017/00946* (2013.01); *A61B 2017/00951* (2013.01); *A61B 2017/0212* (2013.01)

(58) Field of Classification Search
  CPC .......... A61B 17/02; A61B 2017/00946; A61B 2017/00951; A61B 2017/0212
  USPC ....... 600/206; 128/96.1, 100.1, 112.1, 113.1, 128/117.1
  See application file for complete search history.

(56) References Cited

U.S. PATENT DOCUMENTS

| | | | | |
|---|---|---|---|---|
| 4,957,105 A * | 9/1990 | Kurth | ........................ | A61F 5/30 128/107.1 |
| 7,568,966 B2 * | 8/2009 | Abbey | ................. | A41C 3/0057 2/268 |
| 2009/0264709 A1 * | 10/2009 | Blurton | .................. | A61B 17/02 600/206 |
| 2012/0247487 A1 * | 10/2012 | Llinas | .................... | A61B 17/02 128/849 |
| 2013/0133668 A1 * | 5/2013 | Fisher | ....................... | A61F 5/03 128/845 |
| 2013/0149937 A1 * | 6/2013 | Shearer | ................ | A41C 3/0057 450/39 |
| 2015/0296995 A1 * | 10/2015 | Krim | ...................... | A47C 27/15 5/724 |
| 2015/0335322 A1 * | 11/2015 | Galbierz | ................... | A61F 5/37 600/407 |
| 2016/0100975 A1 * | 4/2016 | Korzelius | ................. | A61F 5/37 128/96.1 |

\* cited by examiner

*Primary Examiner* — Pedro Philogene  
*Assistant Examiner* — David C Comstock  
(74) *Attorney, Agent, or Firm* — Tuggle Duggins P.A.; Blake Hurt

(57) ABSTRACT

An apron formed from a gel-infused section of foam with a generally pentagonal shape approximately one inch thick with at least one surface exhibiting a coefficient of friction sufficient to releasably adhere the foam to a portion of human anatomy. The section of foam is suspended between four straps extending beyond the periphery of the foam member, each strap defining a length of at least thirty inches and including longitudinally opposing ends relative to the foam member with hook and loop material that permit the releasable attachment of the straps to a proximal mounting substrate, such as the railings of a conventional surgical bed. A method of manipulating a portion of the human anatomy with such an apron is also included.

14 Claims, 12 Drawing Sheets

PANNUS APRON AND METHOD FOR ACCESSING A SURGICAL SITE

This non-provisional patent application claims all benefits under 35 U.S.C. § 119(e) of U.S. provisional patent application Ser. No. 62/375,729 filed 16 Aug. 2016, entitled "PANNUS APRON AND METHOD FOR ACCESSING A SURGICAL SITE", in the United States Patent and Trademark Office, which is incorporated by reference in its entirety herein.

FIELD OF THE INVENTION

The invention herein pertains to surgical accessories generally, and particularly pertains to an apron to support and manipulate portions of the human anatomy, for example the panniculus, during medical procedures.

DESCRIPTION OF THE PRIOR ART AND OBJECTIVES OF THE INVENTION

Panniculus, or panniculus adipose (commonly referred to as "pannus" in Operating Room [OR] Theaters) is medical terminology describing a dense layer of fatty tissue growth, specifically consisting of subcutaneous fat in the lower abdomen area. It is caused by obesity. The U.S. Government Centers for Disease Control (CDC) latest 2016 figures report an "epidemic" of 38% of adults and 21% of teenagers now "morbidly obese" in the United States. These numbers have increased from 34% and 17%, respectively, in 2012. Using the National Hospital Discharge Survey from 2010, the CDC recorded 51.4 million in-patient surgical procedures (excluding out-patient surgeries) nationwide.

The second most common operation performed were C-sections, with 1.3 million women undergoing this procedure. According to a study conducted in 2009 by nationally acclaimed surgeon Dr. Atul Gawande of Harvard University Medical School, adult Americans average 9.2 surgeries in their lifetimes. Surgeons and staff now face a growing patient that is obese or overweight. Among the many challenges presented by this group is how to prevent the bulk of the panniculus (also called pannus), from interfering with access to the site before, during, and after the procedure. Measures to date commonly used in the OR have included taping the pannus, utilizing medical instrumentation, or having surgical staff physically hold this part of the patient during procedure. Heavy taping of patients can cause skin injuries, and sticky tape residue on the patient and OR bed surfaces, which can harbor microorganisms initiate cross-contamination. Due to reduced elasticity of manual manipulation or taping, compromised respiration is also a very serious possibility. Heavy metal restraints can likewise cause injury and ischemia to skin and soft tissue. Physically manipulating the patient is dangerous to both patient and staff already susceptible to spinal injuries (for example, from heavy patients) in the OR, not to mention increasing the likelihood of exposing the healthcare provider to increased liability during surgical procedures.

Thus, in view of the problems and disadvantages associated with prior art devices and methods of manipulating parts of the human anatomy, the present invention was conceived and one of its objectives is to provide an apron that can easily and efficiently manipulate various portions of the human anatomy, for example during a medical procedure.

It is another objective of the present invention to provide an apron that can releasably manipulate a portion of the human anatomy during a surgical procedure.

It is still another objective of the present invention to provide an apron that can statically and/or frictionally engage a portion of the human anatomy, for example the pannus, during a surgical procedure.

It is yet another objective of the present invention to provide an apron formed from a support member suspended between one or more strap members.

It is a further objective of the present invention to provide an apron formed from a pentagonal piece of gel-infused foam suspended between four hook and loop straps.

It is still a further objective of the present invention to provide an alternate embodiment of an apron formed from a square or rectangular foam member suspended between two strap members.

It is yet a further objective of the present invention to provide a method of manipulating a portion of the human anatomy during a medical procedure including providing an apron with a foam member disposed between at least two straps with hook and loop material ends, statically and/or frictionally engaging the portion of the human anatomy with the foam member, manipulating the portion of the human anatomy in the preferred orientation, for example in a secured position away from a surgical site at a first time point, and affixing the straps to a mounting substrate, for example the rails of a surgical bed, to ensure that the portion of human anatomy does not inadvertently displace and preclude the aforementioned surgical site until the procedure is complete at a second time point.

Various other objectives and advantages of the present invention will become apparent to those skilled in the art as a more detailed description is set forth below.

SUMMARY OF THE INVENTION

The aforesaid and other objectives are realized by providing an apron formed from a gel-infused section of foam defining a generally pentagonal shape approximately one inch thick with at least one surface exhibiting a coefficient of friction sufficient to releasably adhere the foam to a portion of human anatomy. The section of foam is suspended between four straps attached about the periphery of the foam member, each strap defining a length of at least thirty inches and including longitudinally opposing ends relative to the foam member with hook and loop material that permit the releasably attachment of the straps to a proximal mounting substrate, such as the railings of a conventional surgical bed.

A method of manipulating a portion of the human anatomy like the pannus during a medical procedure such as a C-section includes the steps of providing an apron with a foam member disposed between at least two straps with hook and loop material ends, statically and/or frictionally engaging the portion of the human anatomy with the foam member, manipulating the portion of the human anatomy in the preferred orientation, for example lifted in a secured away from a surgical site at a first time point, and affixing the straps to a mounting substrate, for example the rails of a surgical bed, to ensure that the portion of human anatomy does not inadvertently displace and preclude the aforementioned surgical site until the procedure is complete at a second time point.

DETAILED DESCRIPTION OF THE PREFERRED EMBODIMENT AND OPERATION OF THE INVENTION

Figure 1:
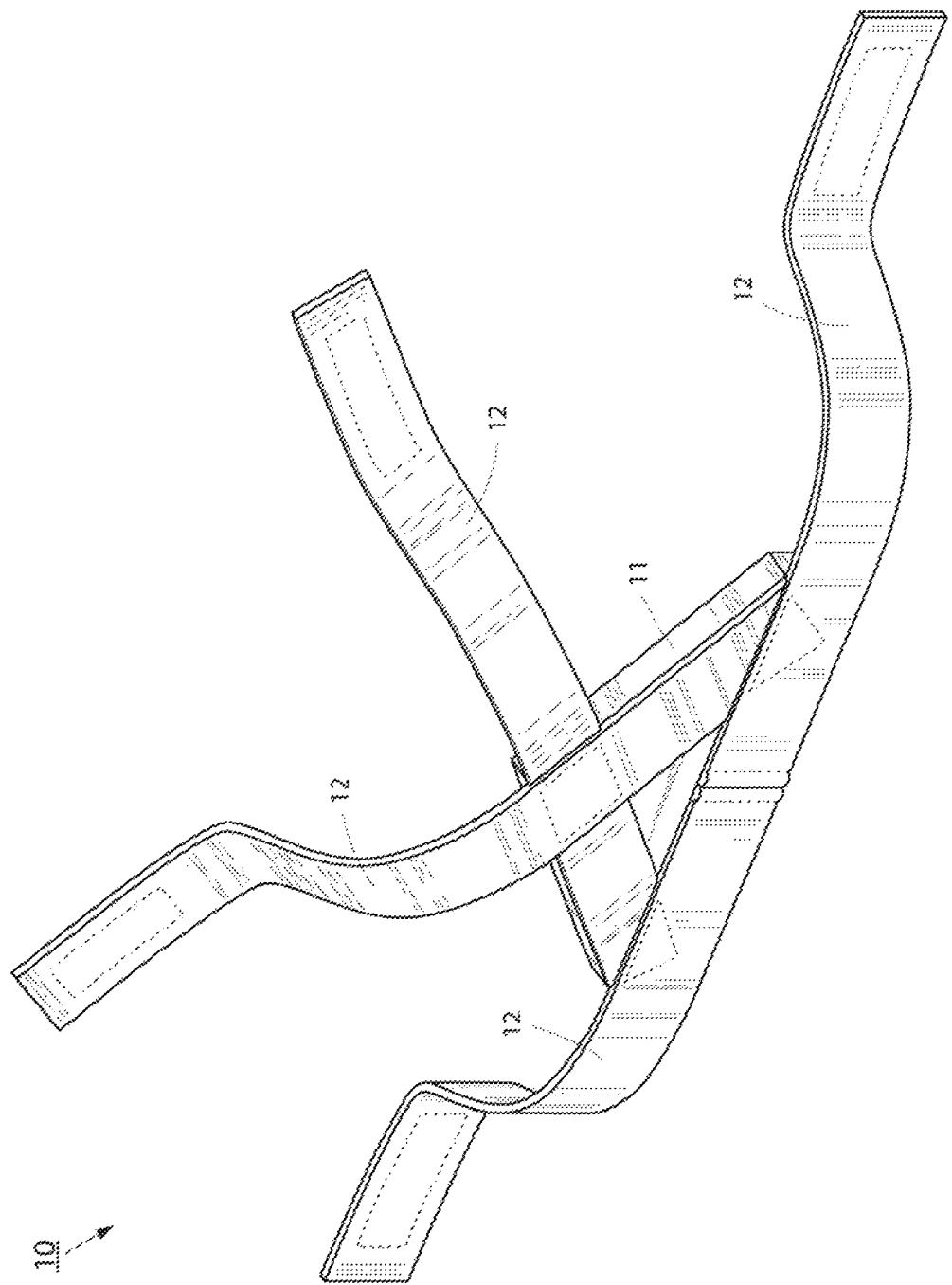
FIG. 1 shows a perspective view of an apron utilized in a surgical environment.

Various exemplary embodiments of the present disclosure are described below. Use of the term "exemplary" means illustrative or buy way of example only, and any reference herein to "the invention" is not intended to restrict or limit the invention to exact features or step of any one or more of the exemplary embodiments disclosed in the present specification. References to "exemplary embodiment", "one embodiment", "an embodiment", "various embodiments", and the like may indicate that the embodiment(s) of the invention so described may include a particular feature, structure, or characteristic, but not every embodiment necessarily includes the particular feature, structure, or characteristic. Further, repeated use of the phrase "in one embodiment", "in an exemplary embodiment", or "in an alternative embodiment" do not necessarily refer to the same embodiment, although they may.

It is also noted that terms like "preferably", "commonly", and "typically" are not utilized herein to limit the scope of the invention or to imply that certain features are critical, essential, or even important to the structure or function of the invention. Rather, these terms are merely intended to highlight alternative or additional features that may or may not be utilized in a particular embodiment of the present invention.

The present invention is described more fully hereinafter with reference to the accompanying figures, in which one or more exemplary embodiments of the invention are Like numbers used herein refer to like elements throughout. The invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limited as to the scope of the invention, and any and all equivalents thereof. Moreover, many embodiments such as adaptations, variations, modifications, and equivalent arrangements will be implicitly disclosed by the embodiments described herein and within the scope of the instant invention.

Although specific terms are employed herein, they are used in a generic and descriptive sense only and not for the purposes of limitation. Unless otherwise expressly defined herein, such terms are intended to be given their broad, ordinary, and customary meaning not inconsistent with that applicable in the relevant industry ad without restriction to any specific embodiment hereinafter described. As used herein, the article "a" is intended to include one or more items. Where only one item is intended, the terms "one and only one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has previously been reduced to practice or that any testing has been performed. Likewise, unless stated otherwise, use of verbs in the past tense (present perfect or preterit) is not intended to indicate or imply that the invention has previously been reduced to practice or that any testing has been performed.

Figure 2:
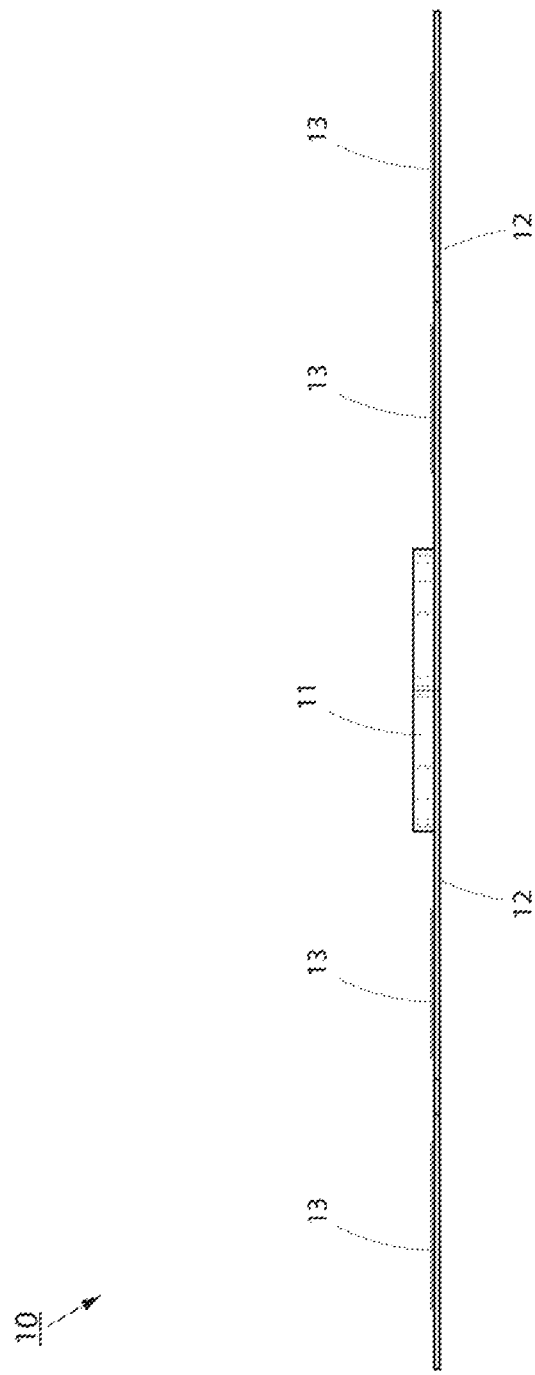
FIG. 2 pictures a top plan view of the apron of FIG. 1.
Figure 3:
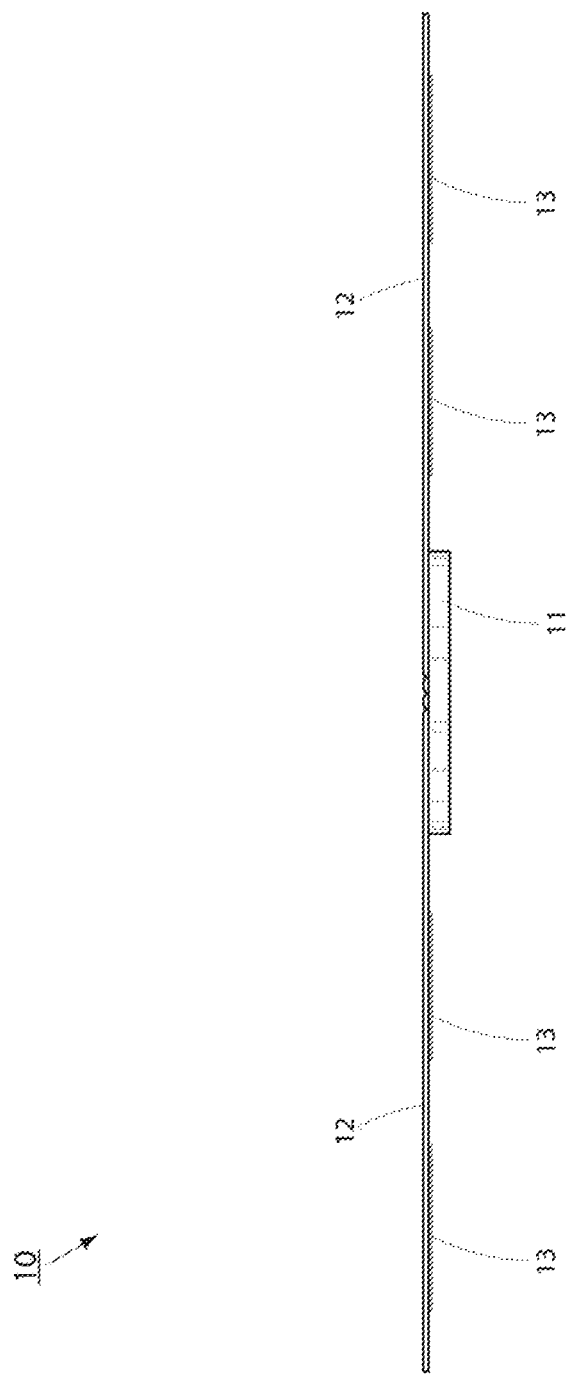
FIG. 3 depicts a bottom plan view of the apron of FIG. 1.
Figure 4:
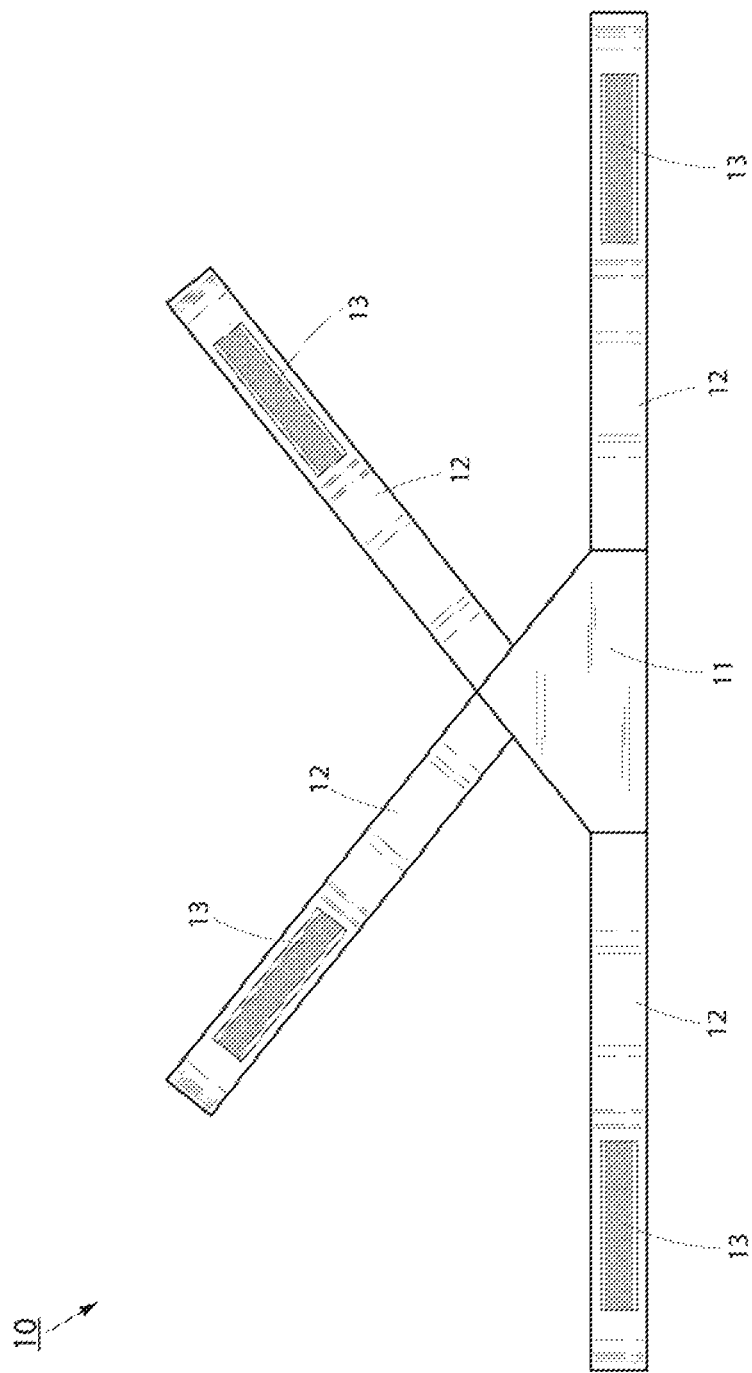
FIG. 4 demonstrates an elevated front view of the apron of FIG. 1.
Figure 5:
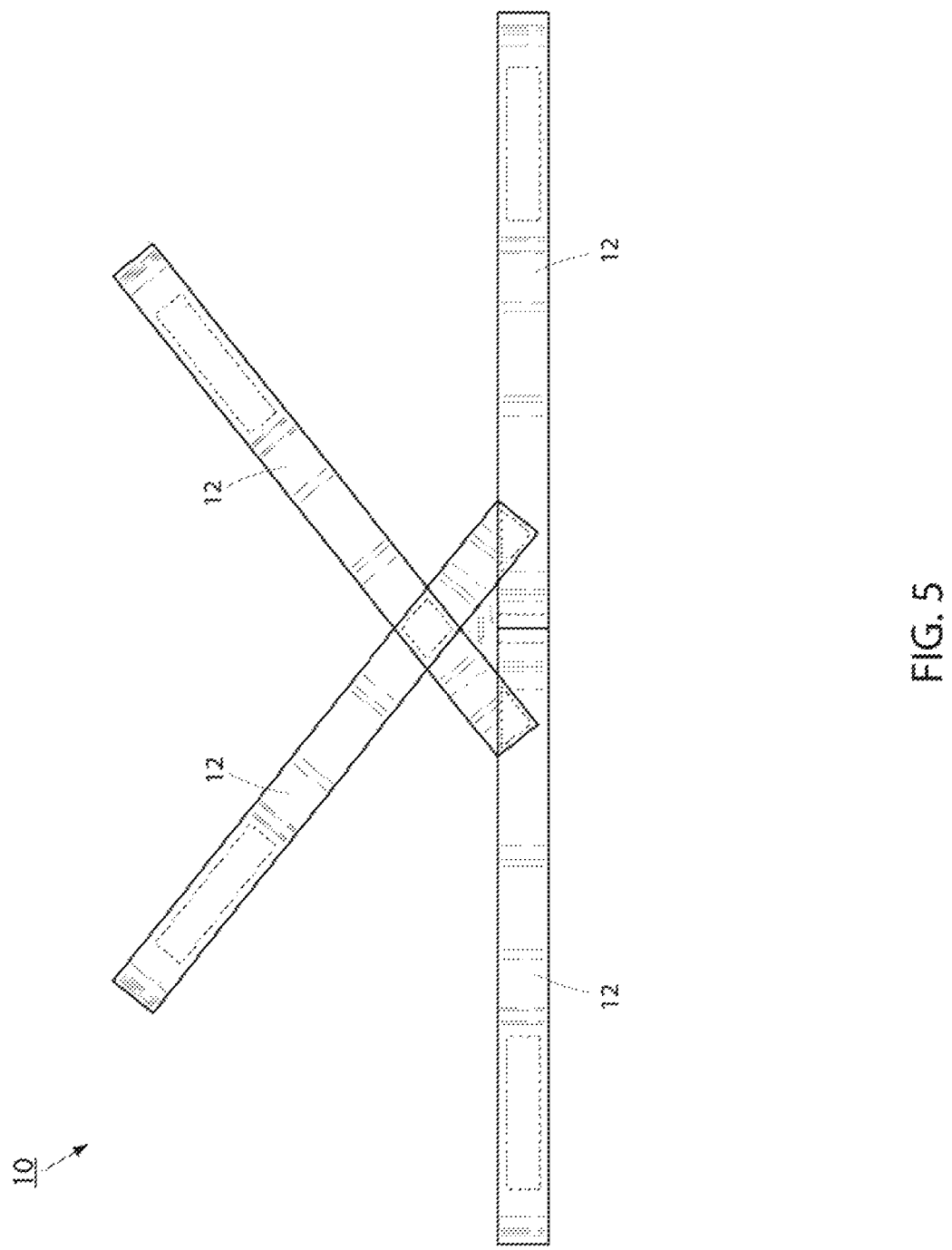
FIG. 5 illustrates an elevated rear view of the apron of FIG. 1.
Figure 6:
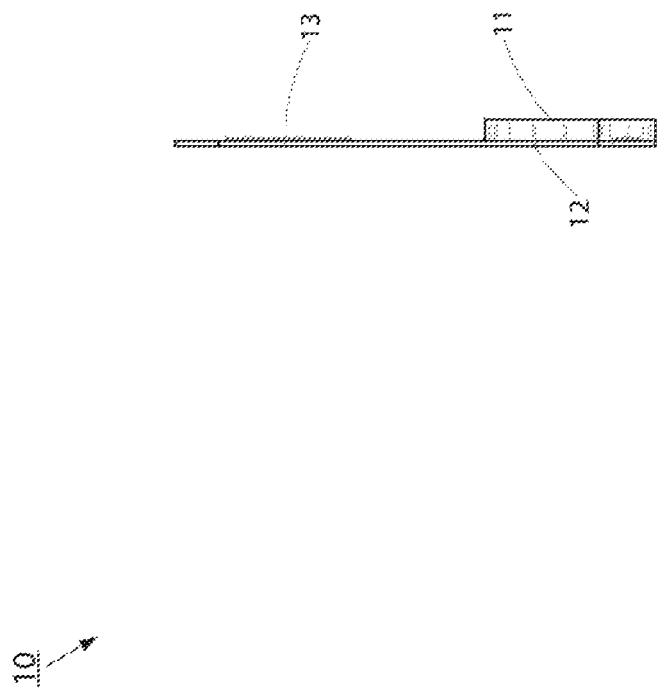
FIG. 6 features an elevated side view of the apron of FIG. 1.

The present disclosure comprises an apron for engaging a part of the human anatomy. a better understanding of the invention and its operation, turning now to the drawings, FIGS. 1-6 show preferred apron 10 including support member 11 carrying a plurality of straps 12 from various vantage points. As should be understood, the term "support member" should be broadly construed to encompass any member that could reasonably be deployed to safely contact and manipulate a portion of the human anatomy for a non-instantaneous amount of time. In an embodiment, the support member includes a surface that is soft and deformable relative to the surface of the human anatomy. In a preferred embodiment, the support member defines a tension that includes a depressible nature that deforms slightly about the geometry of the human anatomy with which it is associated. In an embodiment, the support member is defined by a soft material such as an open-cell or closed-cell foam, and in a preferred embodiment the foam defines at least one surface exhibiting a coefficient of friction sufficient to releasably adhere to a portion of the human anatomy. The preferred support member 11 is formed out of an infused, imbued, or otherwise enhanced foam product that bestows preferred apron 10 with the aforementioned coefficient of friction, as well as additional desirable characteristics. For example, a gel-infused foam product, of the type generally available commercially and sold by Prime Medical under Product No. STP100 (CAS #90009-54-5) demonstrates the preferred coefficient of friction as well as preventing the surface of the human anatomy from becoming overheated during use. This embodiment of foam is a polyurethane foam and is a fully cross-cross-linked reaction product of polyhydroxy polyol, diisocyanate, catalysts, surfactants, pigments, and water. Polyurethane foam is a polymeric material consisting of repeating units of carbon, hydrogen, oxygen, and nitrogen.

Figure 7:
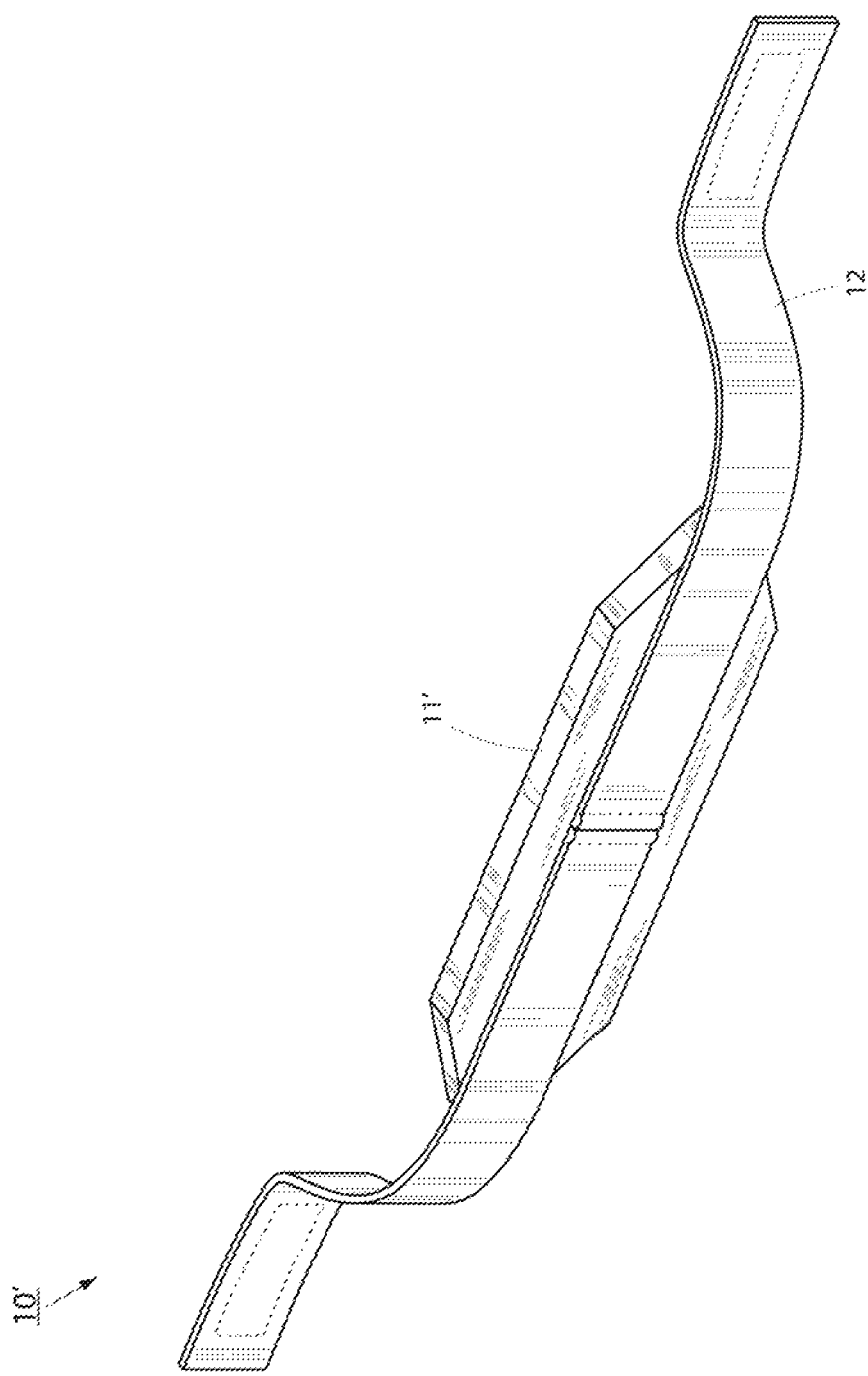
FIG. 7 shows a perspective view of an alternative embodiment of an apron.
Figure 8:
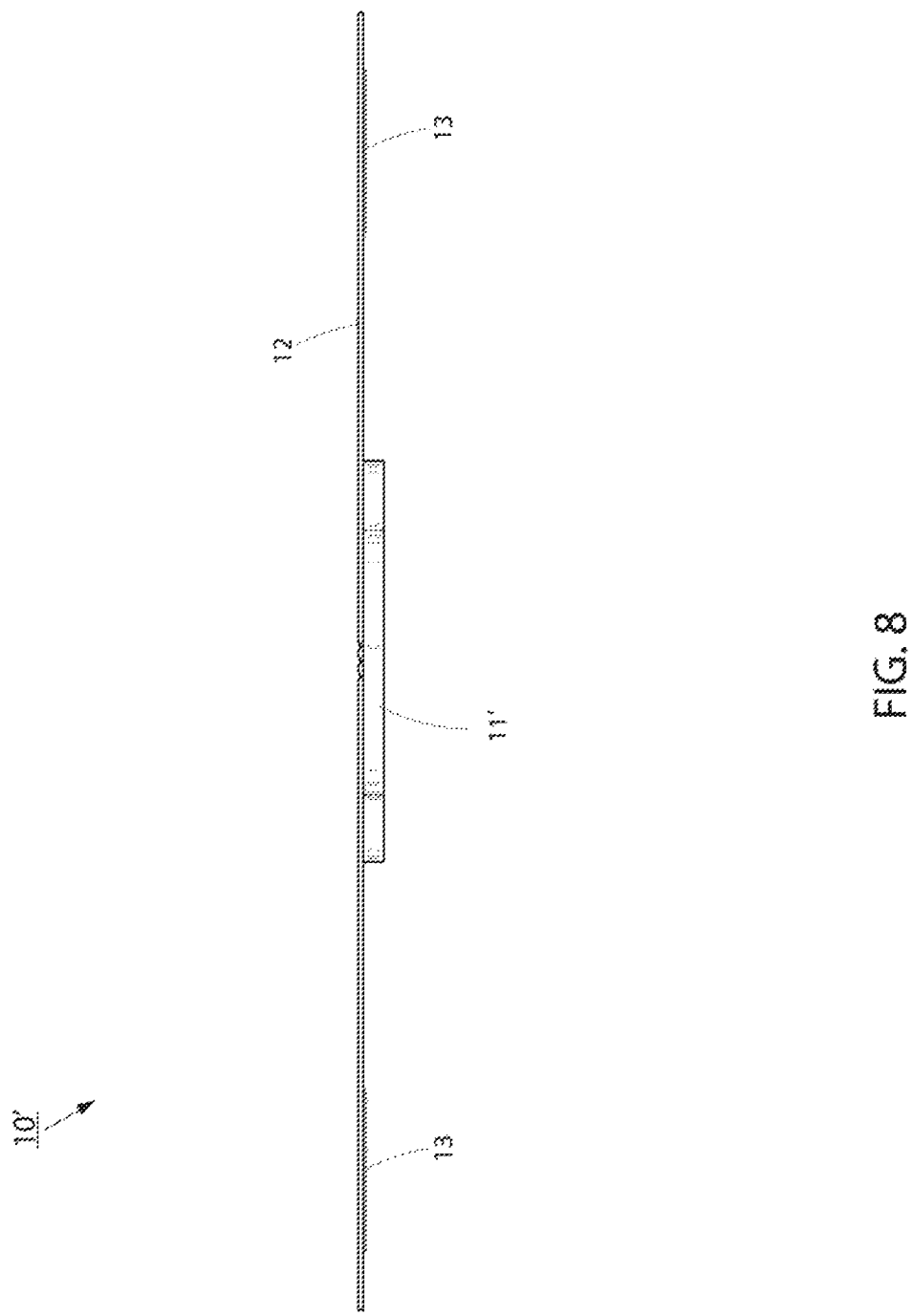
FIG. 8 pictures a top plan view of the apron of FIG. 7
Figure 9:
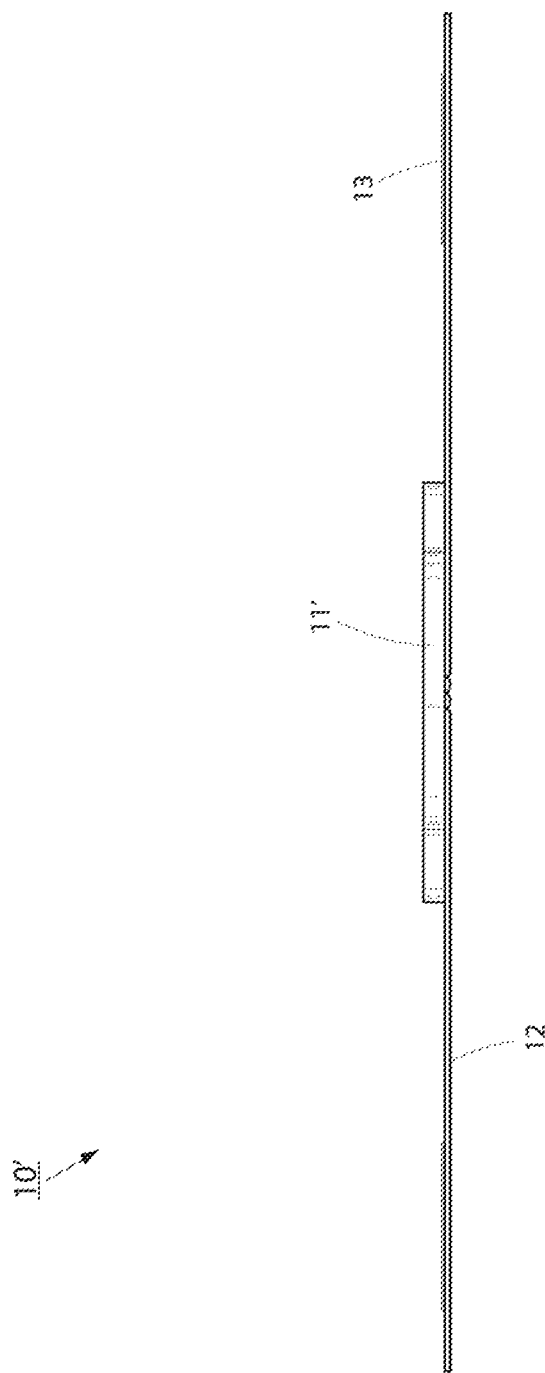
FIG. 9 depicts a bottom plan view of the apron of FIG. 7.
Figure 10:
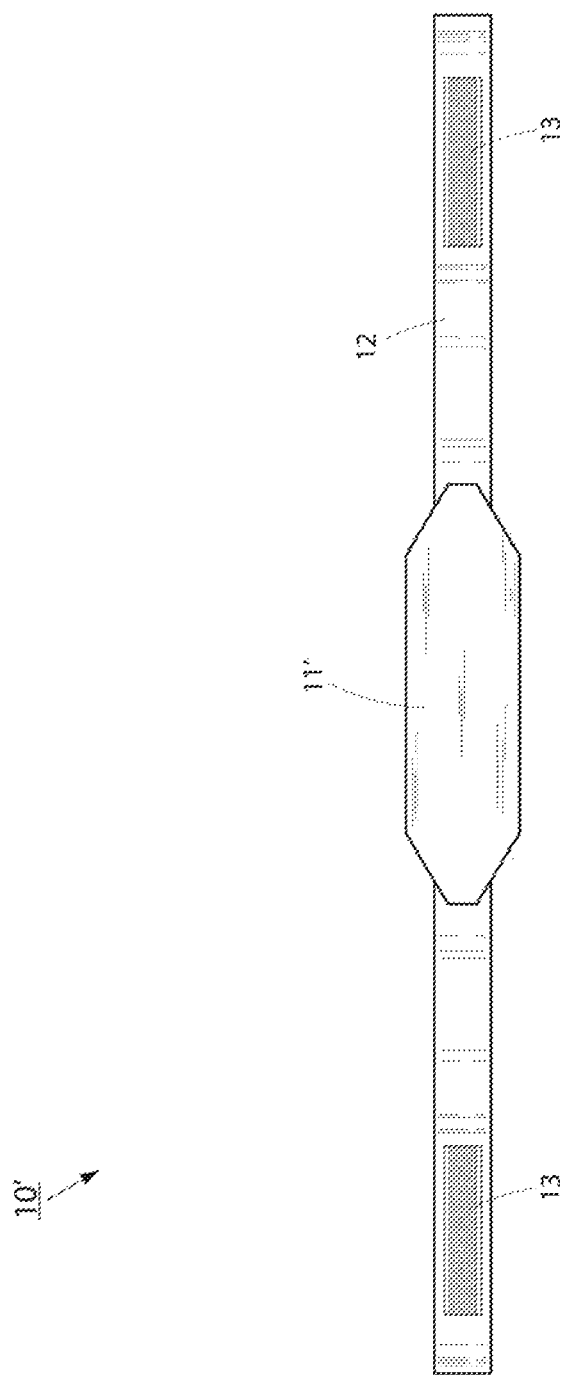
FIG. 10 demonstrates an elevated front view of the apron of FIG. 7.
Figure 11:
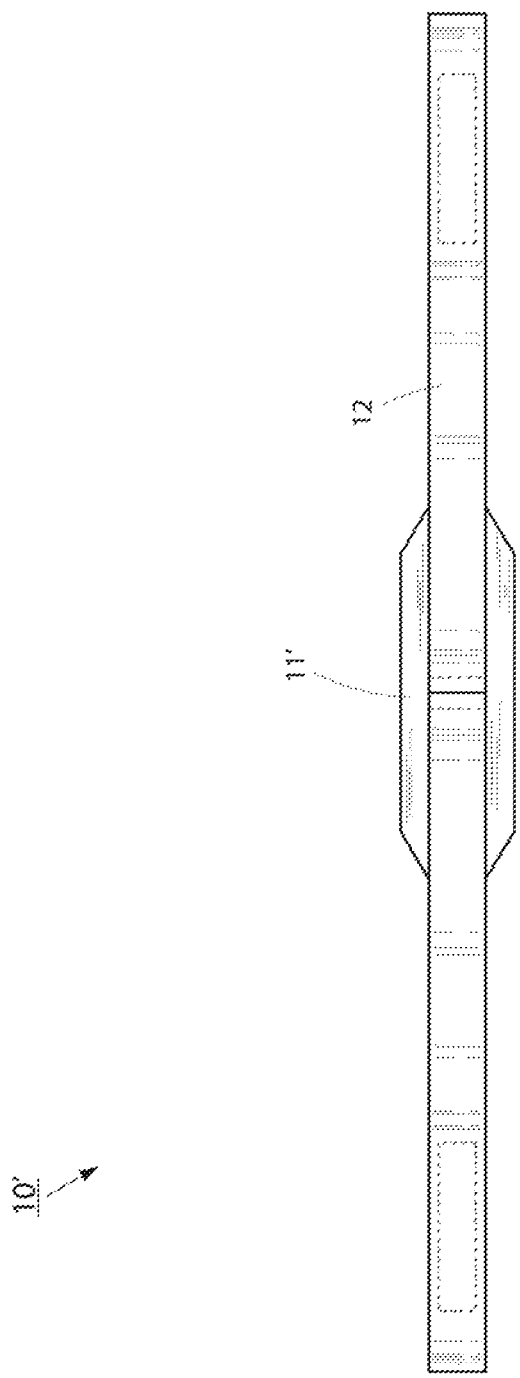
FIG. 11 illustrates an elevated rear view of the apron of FIG. 7.
Figure 12:
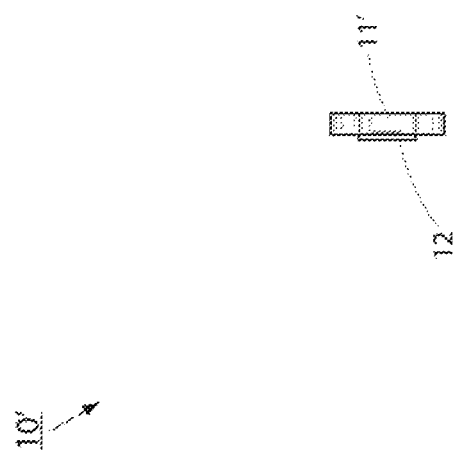
FIG. 12 features an elevated side view of the apron of FIG. 7.

While it should be understood that support member 11 may take any number of regular or irregular polygonal shapes, as well as a variety of typical and atypical circular geometries, preferred support member 11 defines a substantially pentagonal (i.e. generally the same shape as the home plate as known in the game of baseball). This embodiment of support member 11 defines a width of approximately twelve inches (30.48 cm), a length of approximately eight (20.32 cm), and angles bringing the lateral sides of the pentagon to a point defined as approximately forty-five degrees (45°). This configuration of operational variables, while not intended to be limiting, have been experimentally determined to yield a highly flexible solution operant in a wide range of surgical situations. For example, preferred support member 11 may oriented with its longest side facing down (i.e. distal to the head of a patient) during a procedure known as a caesarean section (referred to colloquially as a "C-section"), but the orientation of apron 10 may be rotated ninety degrees (90°) in the event of a lymph node excision and biopsy. As illustrated in FIGS. 7-12, an alternate embodiment of apron 10 (indicated as 10' throughout) may include a support member 11' with a more rectangular shape in comparison to the geometry of support member 11 as described above. One such embodiment of apron 10' includes support member 11' with lateral ends that taper to a point, permitting use of apron 10' in connection with certain features of the human anatomy that may prove inaccessible for support by apron 10.

Embodiments of apron 10 and 10', both illustrated and not, are supported by one or more straps 12 attached to the respective support member and extending past the periphery of said support member to attach to a somewhat distal mounting substrate. In an embodiment, each 12 is a three inch (7.62 cm) wide piece of fabric defining a length of at least thirty inches (76.2 with about 11 inches (27.94 cm) of hook and loop material 13 located at or proximate to a distal end of strap 12 relative to apron 10. In the preferred embodiment, strap 12 is formed from polyester blend fabric with an inner layer of foam of the type generally available commercially sold by Prime Medical under Product No. SS100 (foam insert is S1400) demonstrates sufficient internal structural strength to hold the associated support members 11, 11' in place without damaging tissue and working as a "traction" mode of restraint common to back braces. Straps may be held by surgical personnel, but preferably the straps 12 are wrapped around a somewhat distal mounting substrate, for example the railing of a conventional surgical bed, doubled over upon the strap itself, and held in place as the corresponding hook and loop material mate as is known in the art. It should be understood that straps 12 may also be used with other mounting substrates, regardless of whether or not the mounting substrate is located in an operating room, hospital, or even in a non-medical environment such as the home, and the length of straps 12 should not be construed as a limitation, as it should be understood that the length defined by 12 may vary to accommodate the specific area in which they are used. Similarly, although seeming is indicated in the figures that appears to join two straps 12 together (see examples in 1 and 7), a single strap 12 may be used instead of two such straps without any departure from the spirit or scope of the instant invention.

A method of manipulating a portion of the human anatomy like the pannus during a medical procedure such as a C-section includes the steps of providing an apron 10 with a foam support member 11 disposed between at least two straps 12 with hook and loop material 13 ends, statically and/or frictionally engaging the portion of the human anatomy with the foam support member 11, manipulating the portion of the human anatomy in the preferred orientation, for example lifting the pannus in a secured position away from a surgical site, and affixing the straps 12 to a mounting substrate, for example the rails of a surgical bed, to ensure that the portion of human anatomy does not inadvertently displace and preclude the aforementioned surgical site until the procedure is complete. In this manner, respiration is un-encumbered and the patient does not face trauma from tape removal or shearing. Surgical staff have their hands free, are saved from stooping and lifting portions of the anatomy during the procedure, and the medical provider is relieved of a small amount of liability should the patient or staff member suffer physical repercussions from attempting to manually manipulate the portion of human anatomy during a surgical procedure. Further, in the event that the procedure is a C-section, apron 10, 10' ensures that patient privacy is protected during this (and other) procedure while the patient is awake. Additionally, or in the alternative, while apron 10, 10' has described herein in connection with a particular surgical procedure (namely, a C-section), this should not be construed as a limitation on the functionality of the instant invention, as it should be appreciated that apron 10, 10' may also be utilized in connection with post-operative wound care, burn victim wound care, and a number of other uses which are within the scope of the instant disclosure.

For the purposes of describing and defining the present invention it is noted that the use of relative terms, such as "substantially", "generally", "approximately" and the like, are utilized herein to represent an inherent degree of variability that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as singularly important, necessary, critical, or essential to the invention as a whole unless explicitly described as such. Although only a few of the exemplary embodiments have been described in detail herein, those skilled in the art will readily appreciate that many modifications are possible in these exemplary embodiments without materially departing from the novel teachings and advantages of this invention. The illustrations and examples provided herein are for explanatory purposes and are not intended to limit the scope of the appended claims. Accordingly, all such modifications are intended to be included within the scope of this invention.

I claim:

1. An apron comprising a deformable support member formed from a memory foam and including at least one surface defining a coefficient of friction sufficient to releaseably adhere to a portion of panniculus and configured to support said portion of the panniculus during apron use, the deformable support member positioned between at least two strap members, wherein the strap members define a sufficient length to extend beyond a periphery defined by the deformable support member and attach to a mounting substrate, wherein the memory foam incorporates gel infused throughout the memory foam so as to prevent overheating of the portion of the panniculus during use of the apron.

2. The apron of claim 1, wherein the strap members each includes a portion of hook and loop material.

3. The apron of claim 2, wherein the hook and loop material is positioned at a longitudinal end opposing the deformable support member.

4. The apron of claim 1, wherein the deformable support member defines a pentagonal shape.

5. An apron for securing a portion of the panniculus during a surgical procedure, the apron comprising a deformable support member formed from a memory foam positioned between a plurality of strap members, each strap member includes a portion of hook and loop material positioned at a longitudinal end opposing the deformable support member and defining a length sufficient to extend beyond a periphery defined by the support member and attach to a mounting substrate, wherein the memory foam incorporates gel infused throughout the memory foam so as to prevent overheating of the portion of panniculus during use of the apron, the memory foam including at least one surface defining a coefficient of friction sufficient to releaseably adhere to the portion of panniculus and configured to support said portion of the panniculus during apron use, wherein the deformable support member engages the portion of the panniculus and is manually manipulated into a secured position at a first time point, and wherein the straps are attached to the mounting substrate until the portion of the panniculus no longer need be secured at a second time point.

6. The apron of claim 5, wherein the deformable support member defines a pentagonal shape.

7. The apron of claim 6, wherein the deformable support member defines a width of approximately twelve inches (30.48 cm) and a length of approximately eight inches (20.32 cm).

8. The apron of claim 5, wherein the plurality of strap members define a total of four strap members.

9. The apron of claim 8, wherein each strap member defines a width of three inches (7.62 cm) and a length of at least thirty inches (76.2 cm).

10. The apron of claim 9, wherein each strap member carries about eleven inches (27.94 cm) of hook and loop material positioned at an opposing longitudinal end relative to the apron.

11. A method of securing a portion of the human anatomy during a surgical procedure comprising the steps of:
providing a deformable support member formed from a memory foam including at least one surface defining a coefficient of friction sufficient to releaseably adhere to a portion of panniculus and configured to support said portion of the panniculus during apron us the support member positioned between at least two strap members, wherein the memory foam incorporates gel infused throughout the memory foam so as to prevent overheating of the portion of panniculus during use of the apron
manipulating a portion of the panniculus into a secured position,
engaging the portion of panniculus with the deformable support member, and
securing the strap members to a mounting substrate at a first time point until the portion of panniculus no longer needs be secured at a second time point.

12. The method of claim 11, wherein each strap member includes a portion of hook and loop material positioned at a longitudinal end opposing the deformable support member.

13. The method of claim 12, wherein the deformable support member defines a pentagonal shape.

14. The method of claim 13, wherein the at least two strap members define a total of four strap members.

* * * * *